United States Patent
Dean et al.

(10) Patent No.: US 6,673,319 B2
(45) Date of Patent: Jan. 6, 2004

(54) VESSEL CENTERING SYSTEM AND METHOD

(75) Inventors: Stephen D. Dean, Cary, NC (US); James E. Swon, Chapel Hill, NC (US); C. J. Anthony Fernando, Durham, NC (US)

(73) Assignee: Varian, Inc., Palo Alto, CA (US)

( * ) Notice: Subject to any disclaimer, the term of this patent is extended or adjusted under 35 U.S.C. 154(b) by 510 days.

(21) Appl. No.: 09/798,142

(22) Filed: Mar. 2, 2001

(65) Prior Publication Data

US 2002/0051734 A1 May 2, 2002

Related U.S. Application Data

(63) Continuation-in-part of application No. 09/697,963, filed on Oct. 27, 2000.

(51) Int. Cl.$^7$ .............. B01L 3/02; B01L 3/00; G01N 21/00; G01N 31/00; G04C 1/12; G04C 23/00

(52) U.S. Cl. .............. 422/102; 422/99; 422/100; 422/63; 220/640; 220/655

(58) Field of Search .............. 422/99, 102, 63, 422/100; 220/640, 655, 542, 234, 235, 253, 264

(56) References Cited

U.S. PATENT DOCUMENTS

| | | | | |
|---|---|---|---|---|
| 150,204 A | * | 4/1874 | Sunderland | 220/640 |
| 156,595 A | * | 11/1874 | Roe | 220/640 |
| 269,143 A | * | 12/1882 | Walls | 220/477 |
| 289,974 A | * | 12/1883 | Carpenter | 220/641 |
| 1,179,188 A | * | 4/1916 | Kaminski | 292/256.67 |
| 1,268,550 A | * | 6/1918 | Dunlap | 220/320 |
| 2,575,446 A | * | 11/1951 | Gollong | 220/319 |
| 2,628,739 A | * | 2/1953 | Vischer | 220/305 |
| 2,691,460 A | * | 10/1954 | Barnebey | 220/232 |
| 2,714,469 A | * | 8/1955 | Carlson | 220/320 |

(List continued on next page.)

FOREIGN PATENT DOCUMENTS

| | | |
|---|---|---|
| EP | 0 976 453 A | 2/2000 |
| GB | 992 744 A | 5/1965 |
| GB | 2 001 032 A | 1/1979 |
| WO | WO 92/10294 A1 | 6/1992 |
| WO | WO 98/38478 A | 9/1998 |

OTHER PUBLICATIONS

U.S. Pharmacopeia National Formulary Supplement, USP 23–NF 18, Ninth Supplement, pp. 4660–4669.

Primary Examiner—Jill Warden
Assistant Examiner—B. R. Gordon
(74) Attorney, Agent, or Firm—David Gloekler

(57) ABSTRACT

A vessel centering system comprises a vessel, an annular spacer member, a fastening element, and a first magnetic element. The vessel includes an outer surface and a vessel groove formed on a circumference of the vessel outer surface. The spacer member is fitted in the vessel groove and extends outwardly with respect to the vessel. The first and second lateral end surfaces define a spacing therebetween. The spacer member includes a tangential bore extending along a line generally tangential to a curvature of the spacer member. The fastening element, which could be a screw, is disposed in the tangential bore in engagement with the ring member and extends across the ring spacing. The first magnetic element is supported by or enclosed within the spacer member. A vessel plate with a vessel mounting aperture is structured to accommodate the mounting or installation of the vessel. A second magnetic element is supported by the vessel plate. When the vessel is inserted in the aperture of a vessel plate, magnetic attraction causes the first and second magnetic elements to become aligned with each other, and concentricity between the inner surfaces of the vessel and a shaft extending into the vessel is thereby established.

35 Claims, 13 Drawing Sheets

U.S. PATENT DOCUMENTS

| | | |
|---|---|---|
| 3,092,704 A | 6/1963 | Woody et al. |
| 3,387,741 A * | 6/1968 | Kulaszewski ............... 220/655 |
| 3,559,844 A * | 2/1971 | Schlosberg ................. 220/565 |
| 3,587,700 A * | 6/1971 | Mauer ........................ 220/732 |
| 5,080,232 A | 1/1992 | Leoncavallo et al. |
| 5,190,209 A * | 3/1993 | Gordon et al. ............... 229/5.7 |
| 5,198,109 A | 3/1993 | Hansen et al. |
| 5,296,139 A | 3/1994 | Hansen et al. |
| 5,403,090 A | 4/1995 | Hofer et al. |
| 5,589,649 A | 12/1996 | Brinker et al. |
| 5,639,953 A | 6/1997 | Renslow et al. |
| 6,562,301 B1 * | 5/2003 | Dean et al. ................. 422/102 |

\* cited by examiner

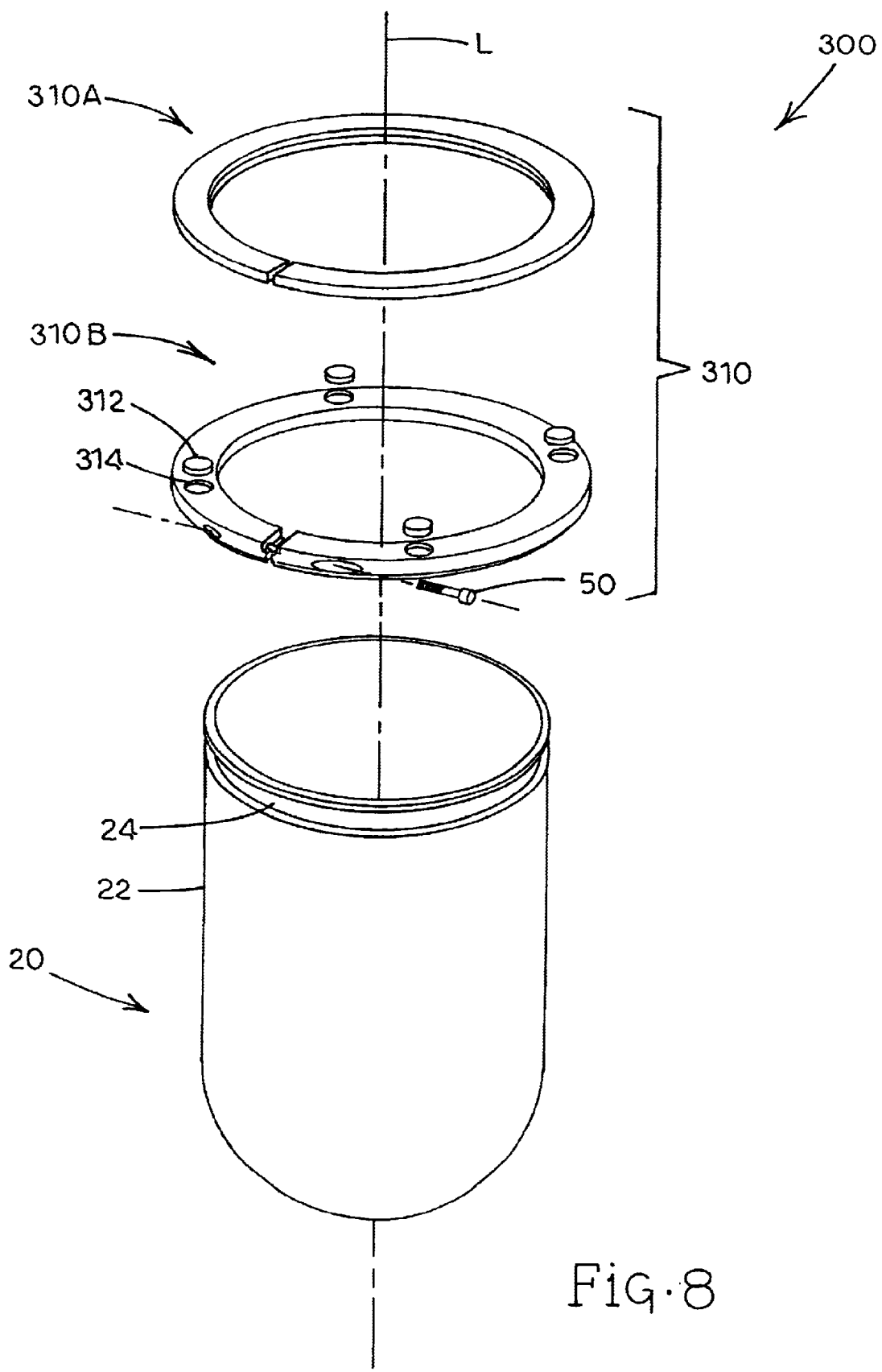

VESSEL CENTERING SYSTEM AND METHOD

CROSS-REFERENCE TO RELATED APPLICATIONS

This is a continuation-in-part of U.S. patent application Ser. No. 09/697,963, filed Oct. 27, 2000, the entire contents of which are herein incorporated by reference.

TECHNICAL FIELD

The present invention generally relates to the preparation or testing of sample substances contained in vessels in which stirring devices or other instruments operate. More particularly, the present invention relates to the centering and alignment of such vessels with respect to the stirring device.

BACKGROUND ART

In the pharmaceutical industry, the stirring or agitation of sample drugs or other substances in vessels is an important step in sample preparation procedures. Examples of such procedures include those performed for the purpose of testing and analyzing the rate at which doses release from pharmaceutical products, such as tablets or capsules, under controlled conditions. The procedural steps, test duration, dissolution medium, and apparatus employed in dissolution tests typically must comply with established, well-recognized guidelines, such as those promulgated by United States Pharmacopeia (USP), in order for the test to be accepted as valid for the specific substance tested.

The apparatus utilized for carrying out dissolution testing typically includes a vessel plate having an array of apertures into which test vessels are mounted. When the procedure calls for heating the media contained in the vessels, a water bath is often provided underneath the vessel plate such that each vessel is at least partially immersed in the water bath to enable heat transfer from the heated bath to the vessel media. In one exemplary type of test configuration (e.g., USP-NF Apparatus 1), a cylindrical basket is attached to a metallic drive shaft and a pharmaceutical sample is loaded into the basket. One shaft and basket combination is manually or automatically lowered into each test vessel mounted on the vessel plate, and the shaft and basket are caused to rotate. In another type of test configuration (e.g., USP-NF Apparatus 2), a blade-type paddle is attached to each shaft, and the pharmaceutical sample is dropped into each vessel such that it falls to the bottom of the vessel. When proceeding in accordance with the general requirements of Section <711> (Dissolution) of USP24-NF19, each shaft must be positioned in its respective vessel so that its axis is not more than 2 mm at any point from the vertical axis of the vessel.

It is therefore an important criterion in certain uses of vessels in which shafts operate that the vessel, and especially its inner surfaces, be aligned concentrically with respect to the shaft, and various approaches have heretofore been taken to assist in meeting this criterion.

One approach is disclosed in U.S. Pat. No. 5,403,090 to Hofer et al., in which at least two embodiments of a vessel aligning structure are provided to lock a standard USP dissolution test vessel into a stable, centered position in a vessel plate relative to a stirring shaft. The vessel is extended through one of the apertures of the vessel plate such that the flanged section of the vessel rests on the top of the vessel plate.

In one embodiment disclosed in U.S. Pat. No. 5,403,090, the vessel aligning structure includes an annular ring having a tapered cylindrical section depending downwardly against the inner surface of the vessel, and an annular gasket surrounding the annular ring. When the vessel aligning structure is pressed onto the vessel, the annular gasket is compressed between the vessel aligning structure and the flanged section of the vessel. A mounting receptacle is secured to the vessel plate adjacent to each aperture of the vessel plate. The vessel aligning structure further includes a horizontal bracket arm which slides into the mounting receptacle and is secured by a wing nut and associated threaded stud. The bracket arm also supports the mounting assembly for the motor and stirring shaft associated with that particular vessel location of the vessel plate.

In another embodiment disclosed in U.S. Pat. No. 5,403,090, the vessel aligning structure includes a plurality of mounting blocks secured to the vessel plate. One mounting block is positioned over each aperture of the vessel plate. Each mounting block includes a tapered cylindrical section depending downwardly against the inner surface of the vessel. The mounting block has two alignment bores which fit onto corresponding alignment pegs protruding upwardly from the vessel plate.

Another approach to vessel alignment is disclosed in U.S. Pat. No. 5,589,649 to Brinker et al, in which each aperture of a vessel plate is provided with three alignment fixtures circumferentially spaced in 120 degree intervals around the aperture. Each alignment fixture includes two semi-rigid alignment arms or prongs extending into the area above the aperture. The flanged section of the vessel rests on top of the alignment arms, such that each pair of alignment arms contact the outer surface of the vessel and the vessel is thereby supported by the alignment fixtures. The alignment arms are described as exerting compressive or "symmetrical spring" forces that tend to center the vessel within the aperture of the vessel plate in which the vessel is installed in order to align the vessel with respect to a stirring element.

Many current vessel centering systems require an unacceptably large footprint around the vessels of a dissolution testing apparatus. As acknowledged by those skilled in the art, a vessel centering system that takes up less area would permit the design of a smaller overall apparatus. The use of a smaller apparatus would be highly desirable in view of the costs associated with building and maintaining pharmaceutical laboratory space.

In addition, current vessel centering systems require the manipulation of two or more components to account for the often poor and/or inconsistent manufacturing tolerances observed in the wall thickness of the extruded glass tubing from which vessels are formed and in the vessel manufacturing process itself. As noted in the publication "Dissolution Discussion Group®," Vol. 1, Section 29.2 (VanKel Technology Group, 1999), glass vessels can be made by hand from large-bore glass tubing. The glass tubing is placed in a rotating device similar to a lathe, heat is applied, and the tubing is separated and sealed to form a hemispheric or other shaped bottom section. Heat is continually applied while the vessel is blown into the desired shape. This labor-intensive process can result in dimensional irregularities in the finished glass product. While plastic vessels are manufactured with better tolerances since they are fashioned from molds, plastic vessels are generally less desirable in many applications due to drug affinity with the surface and slower heat-up rate. Accordingly, there presently exists a need for developing a vessel centering system that adequately addresses the poor tolerance issue.

It is believed that a continuing need exists for practical and effective solutions to providing a vessel centering system. The present invention is provided to address these and other problems associated with the centering and alignment of vessels.

DISCLOSURE OF THE INVENTION

The present invention generally provides a vessel centering or alignment system which establishes and maintains a high degree of concentricity between the inner surfaces of a vessel and its associated shaft. The invention finds advantageous utility in any application in which concentricity is desired as between a vessel and a shaft or other elongate instrument extended into and operating within the vessel. The invention is particularly useful in connection with a sample handling or dissolution apparatus in which one or more vessels are to be installed onto or into some type of a vessel plate or rack. The invention is broadly characterized as providing a vessel which has a structurally distinct, locking flanged section.

According to one embodiment of the present invention, a vessel is adapted for improved centering with respect to a spindle when such vessel is installed in a vessel plate. The vessel comprises a vessel wall, an annular, spacer member, and a fastening or locking element. The vessel wall includes an outer surface and a vessel groove formed on a circumference of the vessel outer surface. The spacer member is fitted in the vessel groove and extends outwardly with respect to the vessel wall, terminating at a first lateral end surface and a second lateral end surface. The fastening element engages the spacer member near the first and second lateral end surfaces.

According to another embodiment of the present invention, the spacer member includes an outer surface, a first lateral end surface, a second lateral end surface, a first tangential bore, and a second tangential bore. The first tangential bore extends from a first outer aperture of the spacer member outer surface to a first inner aperture of the first lateral end surface. The second tangential bore extends from a second outer aperture of the spacer member outer surface to a second inner aperture of the second lateral end surface. The first and second lateral end surfaces define a gap therebetween. The first and second tangential bores extend along a line generally tangential to a curvature of the spacer member. The fastening element is disposed in the first and second tangential bores. The fastening element extends through the first inner aperture, across the gap, and through the second inner aperture, such that the fastening element is movable along the generally tangential line of the first and second tangential bores to engage the spacer member and tighten or lock the spacer member in the vessel groove.

According to yet another embodiment of the present invention, a vessel centering system comprises a vessel, an annular, spacer member, a fastening element, and an elastometric component. The vessel includes an outer surface and a vessel groove formed on a circumference of the vessel outer surface. The spacer member is fitted in the vessel groove and extends outwardly with respect to the vessel, terminating at first and second lateral end surfaces. The first and second lateral end surfaces define a gap therebetween. The spacer member includes a tangential bore and an annular groove. The tangential bore extends along a line generally tangential to a curvature of the spacer member. The fastening element is disposed in the tangential bore in engagement with the spacer member and extends across the gap. The elastometric component is disposed in the annular groove.

According to a further embodiment of the present invention, a vessel centering system comprises a vessel including an outer surface and a vessel groove formed on a circumference of the vessel outer surface, an annular, C-shaped ring member fitted in the vessel groove and extending outwardly with respect to the vessel, and means for tightening the ring member against the vessel groove.

According to an additional embodiment of the present invention, a vessel centering system includes a radial extension element disposed in contact with a ring member fitted to a precision groove cut along an outer circumference of a vessel.

According to yet another embodiment of the present invention, a plurality of biased bearings are substituted for the elastometric component.

According to a still further embodiment of the present invention, the vessel centering system comprises means for presenting a vessel alignment surface for the vessel centering system.

According to an additional embodiment of the present invention, a vessel centering system comprises a vessel plate, a vessel, an annular, spacer member, and a mechanical contact element. The vessel plate includes a vessel plate aperture. The vessel plate aperture includes a first edge and a second edge which cooperatively define an annular shoulder. The vessel extends through the vessel plate aperture, and includes an outer surface and a vessel groove formed on a circumference of the vessel outer surface. The spacer member is fitted in the vessel groove and disposed on the first edge of the vessel plate aperture. The spacer member terminates at a first lateral end surface and a second lateral end surface. The mechanical contact element is disposed in engagement with the spacer member at the first and second lateral end surfaces.

The present invention also provides a method for aligning a vessel concentrically with respect to a shaft extending into the vessel, wherein an annular member is fitted in a groove formed around an outer surface of a flangeless vessel body, thereby forming a multi-piece flanged vessel. The ring member is locked or tightened in the vessel groove by utilizing a fastening element engaging the ring member.

The present invention further provides a method for assembling a vessel centering system. A circumferential groove is formed on an outer surface of a flangeless vessel body. An annular, spacer member can be formed such that the spacer member terminates at a first lateral end surface and a second lateral end surface, with the first and second lateral end surfaces defining a gap therebetween. A tangential bore is formed in the spacer member such that the tangential bore extends along a line generally tangential to a curvature of the spacer member and includes two bore sections opposing each other across the gap of the spacer member. A fastening element is provided and is adapted to engage the spacer member at the tangential bore. The spacer member is fitted in the vessel groove to form a multi-piece flanged vessel. The spacer member is secured in the vessel groove by adjusting a position of the fastening element with respect to the tangential bore.

According to another embodiment of the present invention, a vessel is adapted for improved centering with respect to a spindle or other instrument when installed in a vessel plate. The vessel comprises a vessel wall, a ring member, and a magnetic element. The vessel wall includes an outer surface and a vessel groove formed on a circumference of the vessel outer surface. The ring member is fitted in the vessel groove and extends outwardly with respect to the vessel wall. The magnetic element is supported by the ring member.

According to yet another embodiment of the present invention, the ring member supporting the magnetic element terminates at a gap defined by a first lateral end surface of the ring member and a second lateral end surface of the ring member. A fastening element engages the ring member at the first and second lateral end surfaces.

According to still another embodiment of the present invention, a vessel is adapted for improved centering with respect to a spindle or other instrument when installed in a vessel plate. The vessel comprises a vessel wall, an upper ring member, a lower ring member, a magnetic element, and a fastening element. The vessel wall includes an outer surface and a vessel groove formed on a circumference of the vessel outer surface. The upper ring member is fitted in the vessel groove and extends outwardly with respect to the vessel wall. The upper ring member terminates at a first upper ring member end surface and a second upper ring member end surface. An upper gap is defined between the first and second upper ring member end surfaces. The lower ring member is fitted in the vessel groove in adjacent contact with the upper ring member, and extends outwardly with respect to the vessel wall. The lower ring member terminates at a first lower ring member end surface and a second lower ring member end surface. A lower gap is defined between the first and second lower ring member end surfaces and is substantially aligned with the upper gap. The magnetic element is mounted to the lower ring member and is covered by the upper ring member. The fastening element extends between the first and second end surfaces of the upper and lower ring members.

According to a further embodiment of the present invention, a vessel is adapted to be centered with respect to a spindle or other instrument when installed in a vessel plate. The vessel comprises a vessel wall, a ring member, a magnetic element, and a fastening element. The vessel wall includes an outer surface and a vessel groove formed on a circumference of the vessel outer surface. The ring member is fitted in the vessel groove and extends outwardly with respect to the vessel. The ring member includes an outer surface, a first lateral end surface, a second lateral end surface, and first and second tangential bores. The first tangential bore extends from a first outer aperture of the ring member outer surface to a first inner aperture of the first lateral end surface, and the second tangential bore extends from a second outer aperture of the ring member outer surface to a second inner aperture of the second lateral end surface. The first and second lateral end surfaces define a gap therebetween. The first and second tangential bores extend along a line generally tangential to a curvature of the ring member. The magnetic element is supported by the ring member. The fastening element is disposed in the first and second tangential bores. The fastening element extends through the first inner aperture, across the gap, and through the second inner aperture, such that the fastening element is movable along the generally tangential line of the first and second tangential bores in engagement with the ring member.

According to a still further embodiment of the present invention, a vessel centering system comprises a vessel including an outer surface and a vessel groove formed on a circumference of the vessel outer surface, an annular spacer member fitted in the vessel groove and extending outwardly with respect to the vessel, a magnetic element supported by the spacer member, and means for tightening the spacer member against the vessel groove. The tightening means can include a fastening element engaging a bore of the spacer member.

According to a yet further embodiment of the present invention, a vessel centering system comprises a vessel plate, a vessel, an annular spacer member, and first and second magnetic elements. The vessel plate includes the first magnetic element, and also includes a vessel plate aperture. The vessel extends through the vessel plate aperture. The vessel includes an outer surface and a vessel groove formed on a circumference of the vessel outer surface. The annular spacer member is fitted in the vessel groove and is disposed on the vessel plate. The second magnetic element is supported by the spacer member, and is aligned with the first magnetic element by magnetic attraction.

According to an additional aspect of the present invention, a method is provided for aligning a vessel concentrically with respect to a shaft extending into the vessel. A flangeless vessel body is provided, which has a groove formed circumferentially around an outer surface of the vessel. An annular spacer member is fitted in the vessel groove. The spacer member includes a first magnetic element. The vessel body and the spacer member cooperatively form a multi-piece flanged vessel. The spacer member is secured in the vessel groove by utilizing a fastening element engaging the spacer member.

It is therefore an object of the present invention to provide a vessel centering system adapted to easily and quickly achieve concentricity as between the inner surfaces of a vessel and a stirring element or other spindle or shaft-type instrument inserted into the vessel.

It is another object of the present invention to provide a multi-piece flanged vessel wherein the flanged section is a separate, removable structural component.

It is a further object of the present invention to provide a flanged vessel wherein the flanged portion can be locked onto the vessel wall or removed therefrom.

It is yet another object of the present invention to provide a vessel adapted for improved installation with a vessel plate, such as a vessel plate typically provided with a liquid handling apparatus or dissolution testing apparatus.

Some of the objects of the invention having been stated hereinabove, other objects will become evident as the description proceeds when taken in connection with the accompanying drawings as best described hereinbelow.

BRIEF DESCRIPTION OF THE DRAWINGS

FIG. 8 is an exploded, perspective view of a vessel centering system according to another embodiment of the present invention in which magnets are utilized;

DETAILED DESCRIPTION OF THE INVENTION

Figure 1:
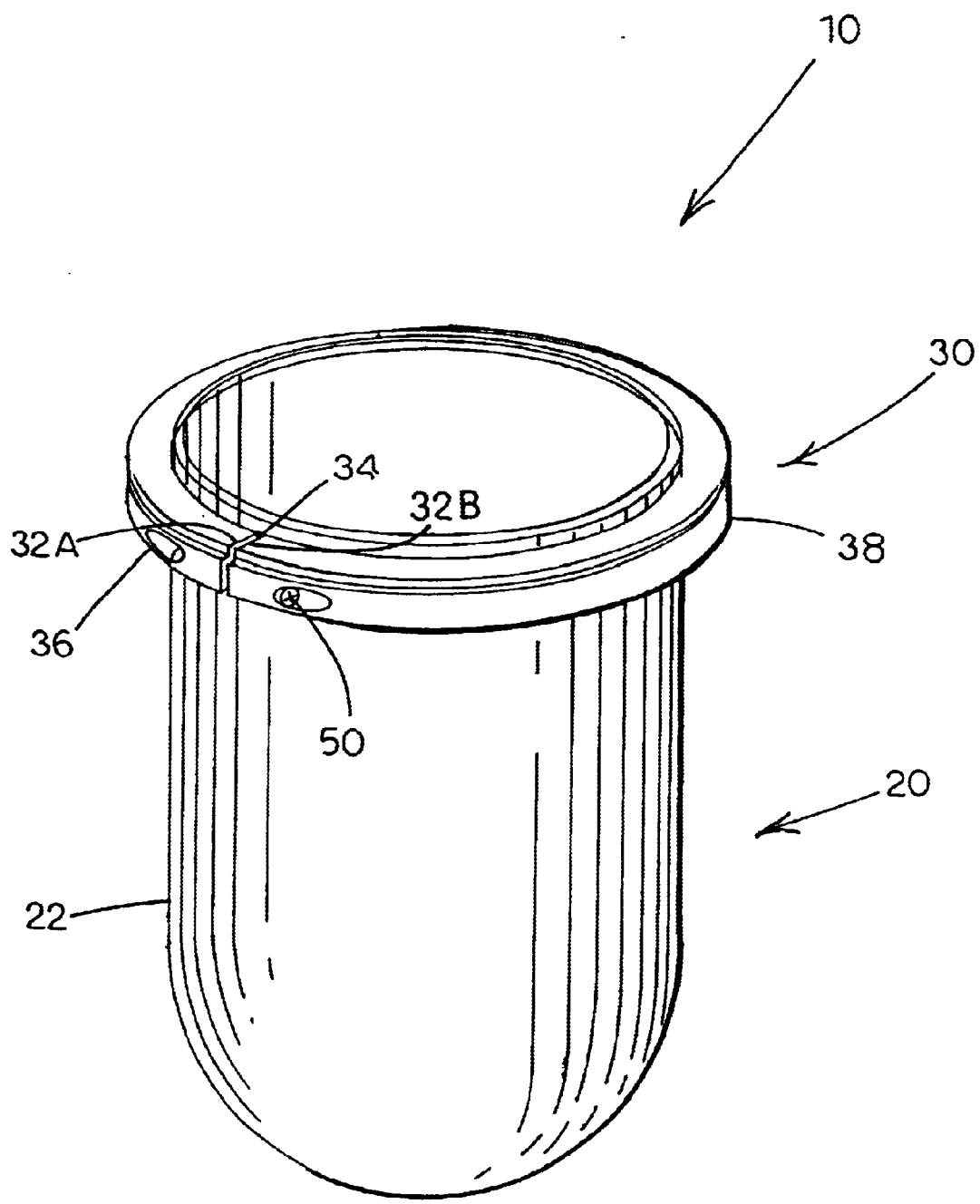
FIG. 1 is a perspective view of a vessel centering system provided according to the present invention.
Figure 2:
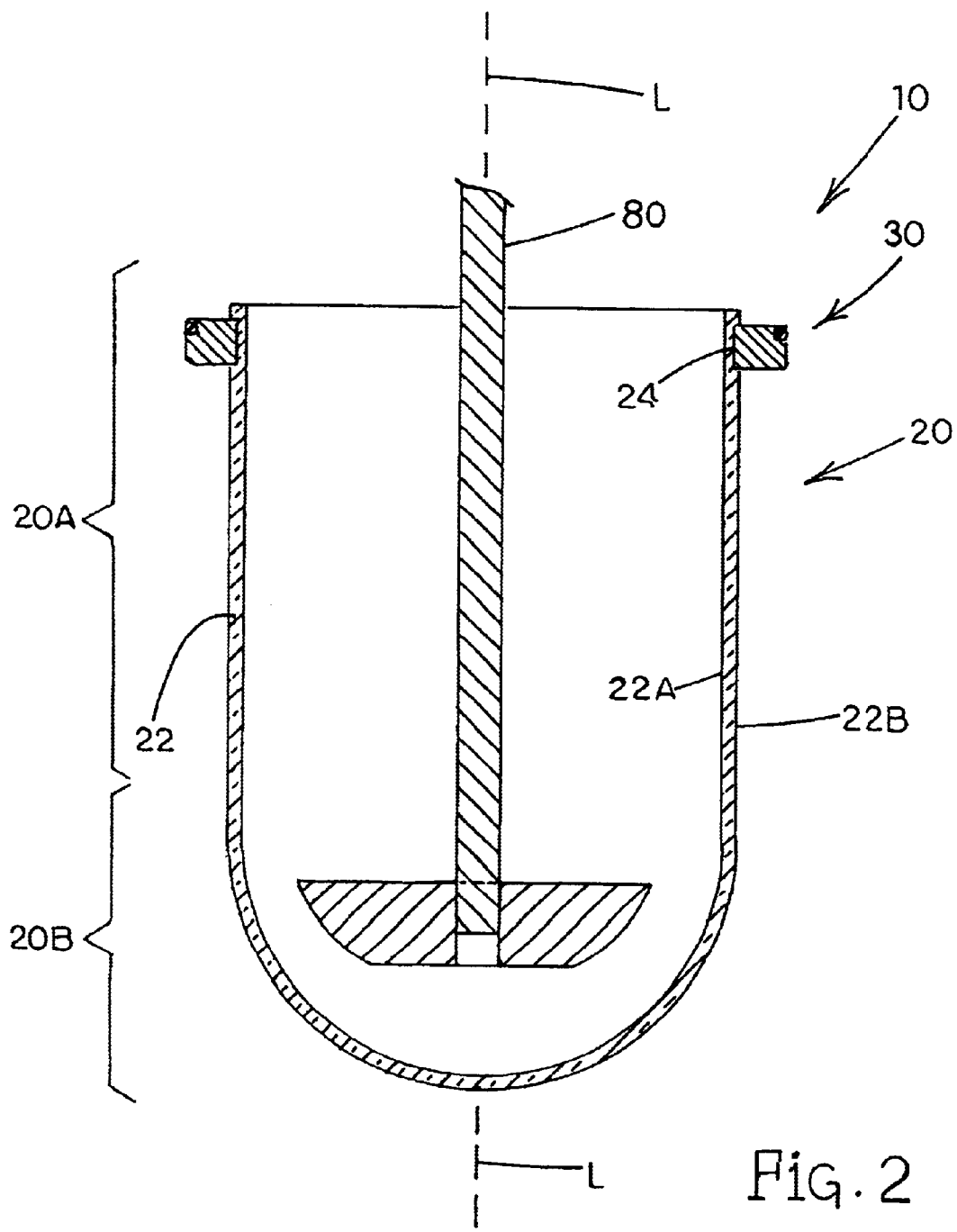
FIG. 2 is a vertical cross-sectional view of the vessel centering system illustrated in FIG. 1, and additionally of a shaft-based instrument operable in conjunction with the vessel centering system.
Figure 4:
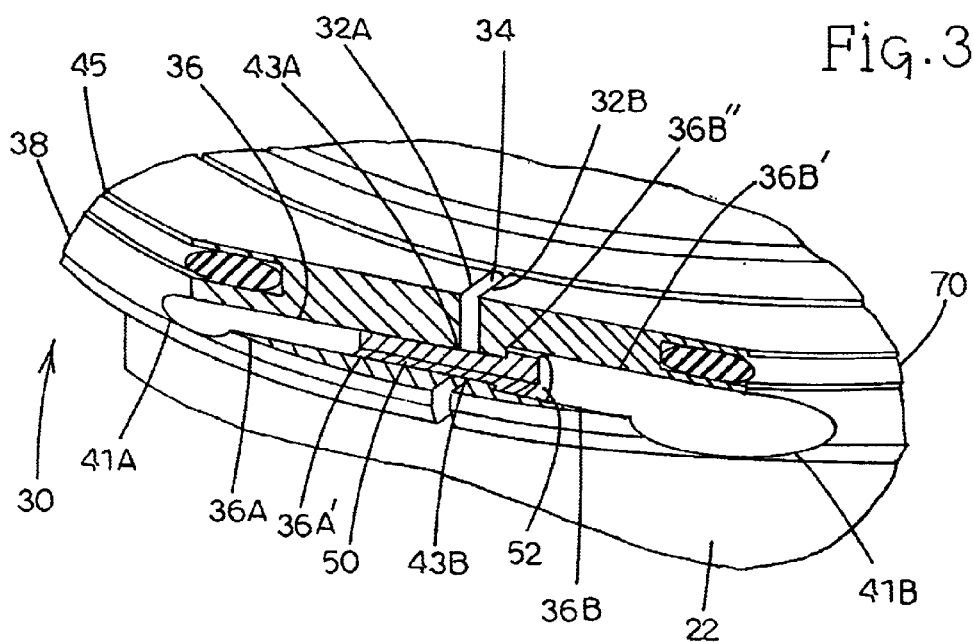
FIG. 4 is a detailed perspective and partial cutaway view of the vessel centering system illustrating an inner cross-sectional portion of a ring member provided according to the present invention.

Referring to FIGS. 1 and 2, a vessel centering/alignment system generally designated 10 is provided in accordance with the present invention, and is particularly suited for use in conjunction with a dissolution testing apparatus. Broadly stated, vessel centering system 10 includes a vessel generally designated 20 and a vessel alignment ring generally designated 30. Vessel 20 includes a vessel wall 22 having an inner surface 22A and an outer surface 22B. In the preferred embodiment, vessel 20 is a modification of a standard USP vessel having, for example, a lateral cylindrical section 20A and a bottom hemispherical section 20B (although bottom section 20B could be flat, dimpled, or have some other suitable configuration). Vessel alignment ring 30 serves as the flanged section of vessel 20, yet preferably is provided as a separate component such that vessel 20 could be characterized as having a multi-piece design. Vessel 20 is preferably constructed of a glass (or other transparent) material, and alignment ring 30 is preferably constructed of a polymeric material such as PVC or TEFLON material. Alignment ring 30 is C-shaped, and thus terminates at two lateral end surfaces 32A and 32B separated by a gap 34, as best shown in FIG. 4. As particularly shown in FIG. 2, an annular groove 24 is precision cut or ground into outer surface 22B of vessel wall 22 and is concentric with inner surface 22A. One way to properly form annular groove 24 relative to inner surface 22A is to chuck or attach a lathe to inner surface 22A, such that the lathe moves about a central, longitudinal axis L of vessel 20 as annular groove 24 is cut.

Alignment ring 30 is mounted in this annular groove 24. Annular groove 24 removes the irregularities that may be inherent in the extruded glass tubing or result from the glass manufacturing process. As will also become apparent from the present disclosure, vessel centering system 10 ensures concentricity as between inner surface 22A of vessel 20 and an instrument operative within vessel 20 such as a shaft-based agitator device 80, or any other device adapted for extension into vessel 20 along central axis L thereof. In addition, alignment ring 30 is designed for easy removal from vessel 20 either manually or by using a tool.

Referring to FIG. 4, a fastening or clamping means such as a tangential screw 50 is employed to squeeze, tighten, or otherwise secure alignment ring 30 into annular groove 24 and around the periphery of vessel 20, thus effectively locking alignment ring 30 into position with respect to vessel 20. To accommodate tangential screw 50, a tangential screw bore 36 is formed through the body of alignment ring 30 along a direction generally tangential to the curvature of alignment ring 30. In the exemplary embodiment shown, tangential bore 36 spans across gap 34 between lateral end surfaces 32A and 32B such that tangential bore 36 includes two generally aligned bore sections 36A and 36B. First bore section 36A extends between an outer surface 38 of alignment ring 30 and first lateral end surface 32A, and opens at an outer aperture 41A of outer surface 38 and at an inner aperture 43A of first lateral end surface 32A. Similarly, second bore section 36B extends between outer surface 38 of alignment ring 30 and second lateral end surface 32B, and opens at another outer aperture 41B of outer surface 38 and at an inner aperture 43B of second lateral end surface 32B.

It will be understood that tangential screw 50 is but one type of fastening element which could be adapted to operate within the context of the present invention. Other fasteners or clamps, now or later developed, may be found suitable for serving the same purpose or function as that of tangential screw 50.

Preferably, second bore section 36B includes an enlarged diameter section 36B' to define a shoulder 36B" within second bore section 36B, and first bore section 36A includes a threaded section 36A' adapted to mate with the threads of tangential screw 50. In this manner, a suitable tool (not shown) can be inserted through second outer aperture 41B into second bore section 36B and brought into operative engagement with a head portion 52 of tangential screw 50. It will be understood that means other than a tool could be used to rotate tangential screw 50 or otherwise adjust its position relative to tangential bore 36. Because tangential screw 50 is forced into movable engagement with threaded section 36A' of first bore section 36A and its head portion 52 is forced into engagement with shoulder 36B" of second bore section 36B, rotation of tangential screw 50 acts to adjust the position of tangential screw 50 with respect to tangential bore 36, thereby adjusting the width of gap 34 and altering the outermost diameter and profile of alignment ring 30 to tighten or lock alignment ring 30 in place.

Figure 3:
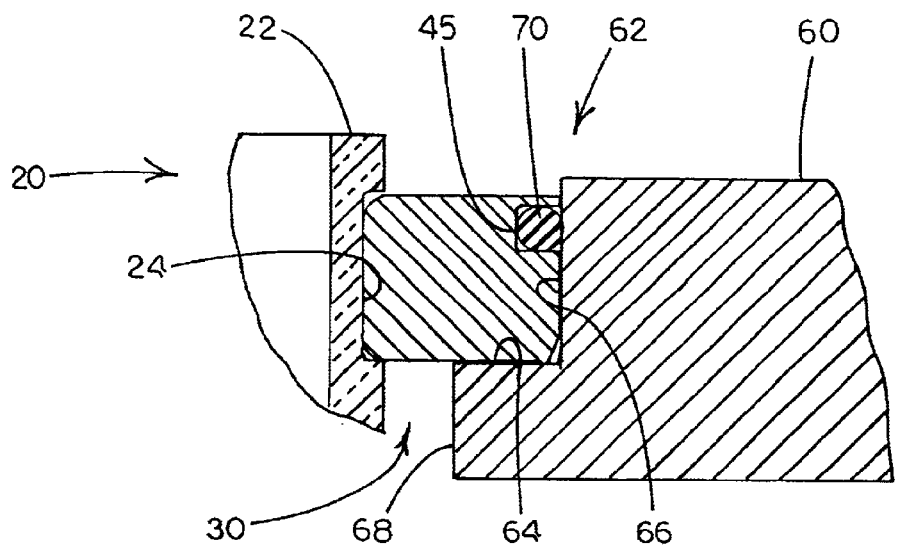
FIG. 3 is a detailed vertical cross-sectional and partial cutaway view of the vessel centering system installed on a vessel plate according to the present invention.

Referring to FIG. 3, vessel 20 is adapted to be installed in a vessel plate 60. In accordance with the present invention, vessel plate 60 includes one or more apertures, generally designated 62, which are modified to receive vessel 20. In this respect, modified vessel plate 60 could be considered as forming a part of vessel centering system 10. Each vessel plate aperture 62 is defined by a first edge 64 and a second edge 66 of vessel plate 60, which together define an annular shoulder 68 with which alignment ring 30 engages. Preferably, alignment ring 30 includes an annular groove 45, and a removable resilient or elastometric component 70 such as an annular gasket or O-ring (or other elastometric centering means) is fitted into annular groove 45 concentric with alignment ring 30 and vessel 20.

It can be seen that alignment ring 30 serves as a spacer means for bridging the annular gap presented between precision annular groove 24 and second edge 66 of vessel plate 60, and for establishing the concentricity of vessel 20 with respect to longitudinal axis L. At the same time, elastometric component 70 serves as an outer frictional surface or radial extension of vessel 20, and as a means for spanning the small (and potentially variable) annular gap presented between alignment ring 30 and the inner diameter of aperture 62 (i.e., second edge 66 of vessel plate 60). The use of elastometric component 70 thus enhances the establishment of the concentricity of vessel 20 with respect to longitudinal axis L and agitator device 80, rather than serving the conventional role of a seal.

It can also be seen that the frictional outer surface presented by elastometric component 70 prevents vertical displacement of vessel 20 out of its installed position in vessel plate 60. This latter feature is advantageous in the situation where vessel or vessels 20 of vessel plate 60 have been immersed in a water bath, and the media content in one or more vessels 20 has been reduced to the point where vessel or vessels 20 are forcibly displaced upwardly due to buoyancy effects. Elastometric component 70 prevents its associated vessel 20 from "popping out" of vessel plate 60 in response to such buoyancy effects.

Figure 5:
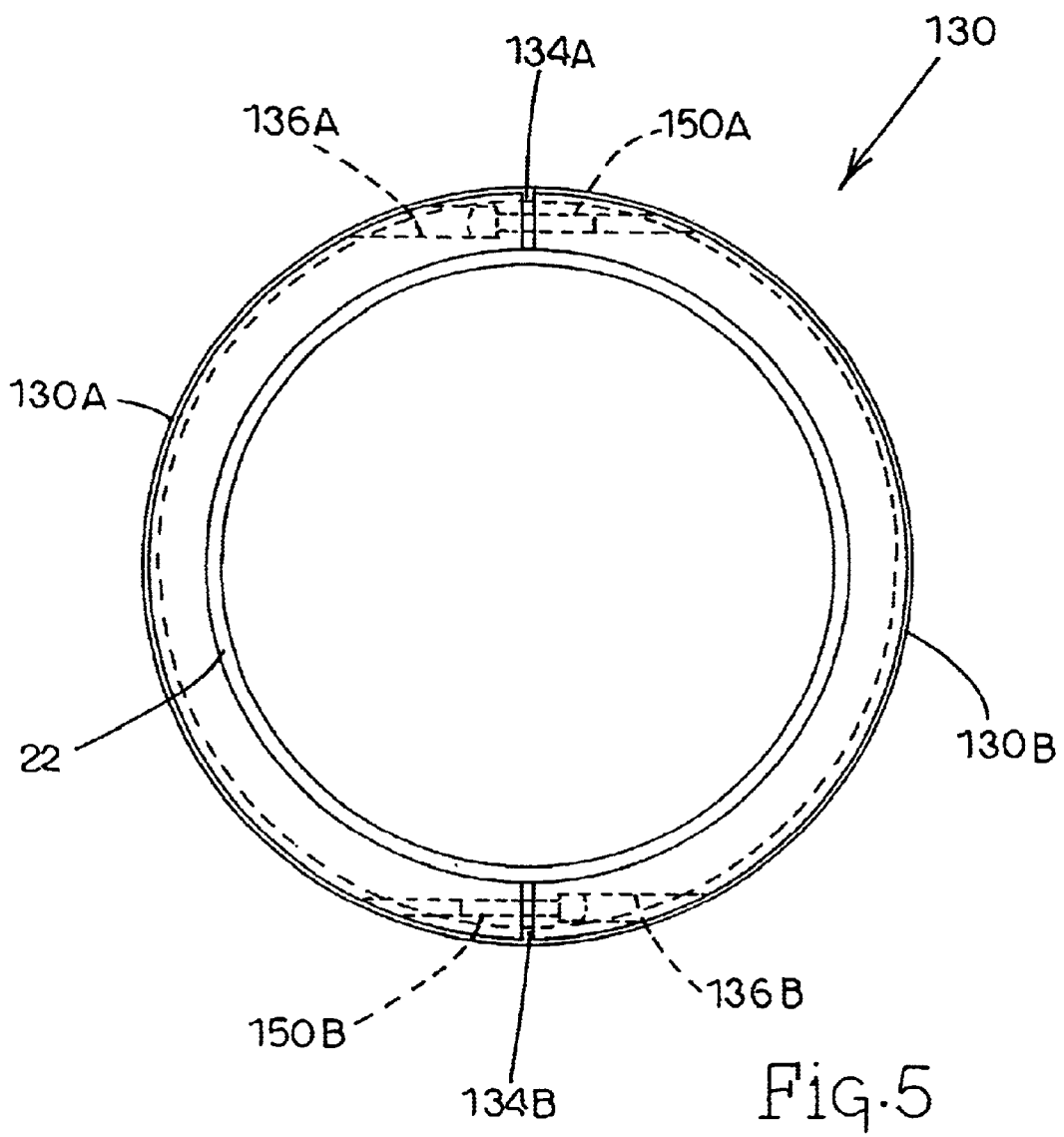
FIG. 5 is a top plan view of a spacer member or removable flange piece according to an embodiment of the present invention.

Referring to FIG. 5, an alternative embodiment of an alignment ring, generally designated 130, is illustrated according to the invention. FIG. 5 illustrates that the alignment ring of the present invention, as a spacer means and a means for ensuring concentricity, can assume configurations other than a C-ring such as alignment ring 30 discussed hereinabove. By way of example in FIG. 5, alignment ring 130 includes two or more segments 130A and 130B and accordingly defines two or more gaps 134A and 134B. In addition, two or more tangential bores 136A and 136B (with generally aligned bore sections) and corresponding tangential screws 150A and 150B are provided.

Figure 6:
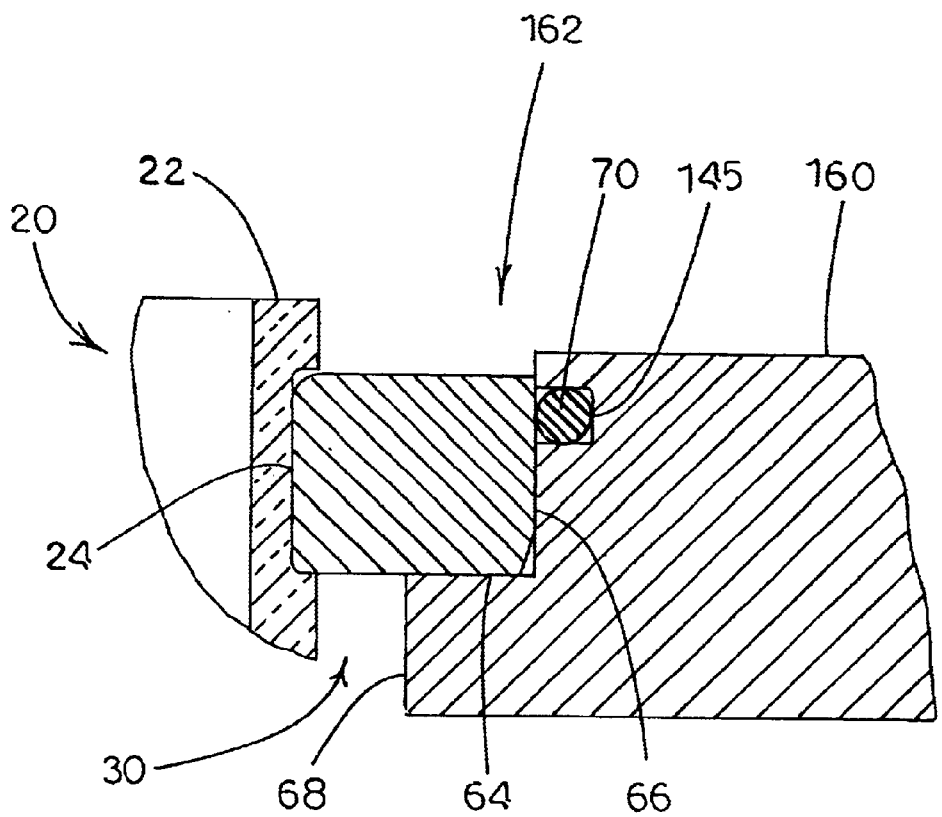
FIG. 6 is a detailed vertical cross-sectional and partial cut-away view of an alternative embodiment of the vessel centering system installed in a vessel plate.

Referring to FIG. 6, an alternate embodiment of the present invention is provided wherein an annular groove 145 is formed in a vessel plate aperture, generally designated 162, instead of being formed in alignment ring 30 shown in FIG. 3 (or alignment ring 130 shown in FIG. 5). Annular groove 145 extends into second edge 66 of a modified vessel plate 160. Elastomeric component 70 is fitted into annular groove 145. In this manner, elastomeric component 70 serves as an inner frictional surface of vessel plate aperture 162 to perform its gap-spanning and concentric positioning functions.

Figure 7A:
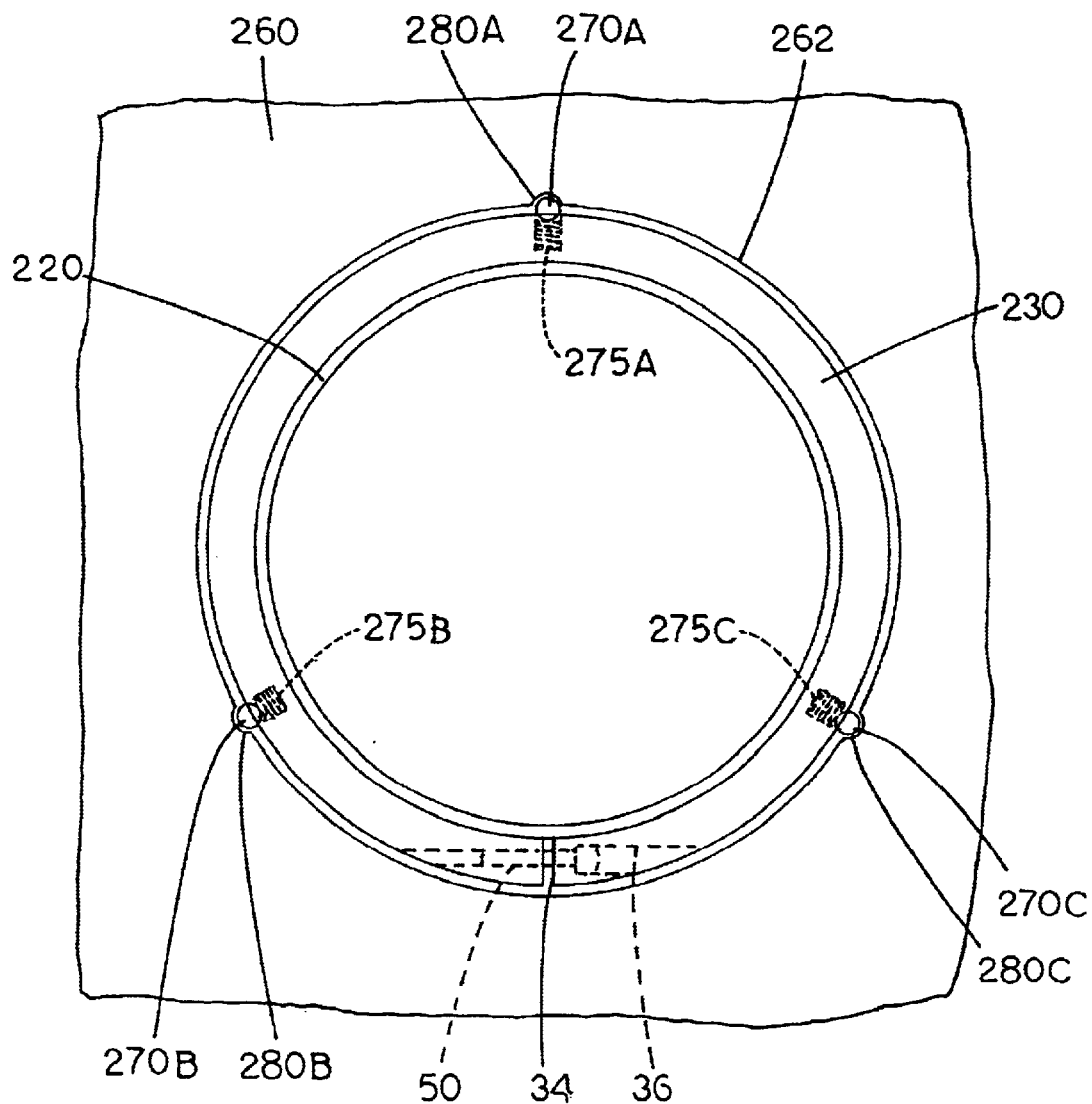
FIG. 7A is a top plan view of the vessel centering system according to one embodiment of the present invention wherein biased radial members are utilized.

Referring to FIG. 7A, an alternative embodiment of the present invention is provided wherein the gap-spanning and concentric positioning means take the form of radially outwardly biased (such as by spring loading) bearings or dimples 270A, 270B and 270C, instead of elastomeric component 70. By way of example, three bearings 270A, 270B and 270C are provided and are circumferentially spaced 120° from each other. Each bearing 270A, 270B and 270C and its associated biasing mechanism 275A, 275B and 275C are supported in or by a flanged section 230 (which can be integrally manufactured with a vessel 220 or provided as a separate, removable component as in other embodiments discussed above). Hence, bearings 270A, 270B and 270C extend outwardly from flanged section 230 and are biased to make contact with a vessel plate aperture 262 of a vessel plate 260 to establish the concentricity of vessel 220. In this embodiment, neither flanged section 230 nor aperture 262 require an annular gap 45 (see FIG. 3) or 145 (see FIG. 6). However, conformingly-shaped depressions or recesses 280A, 280B and 280C may be provided along the inner diameter of aperture 262 at the respective locations of bearings 270A, 270B and 270C to at least partially receive the outer profile of bearings 270A, 270B and 270C.

Figure 7B:
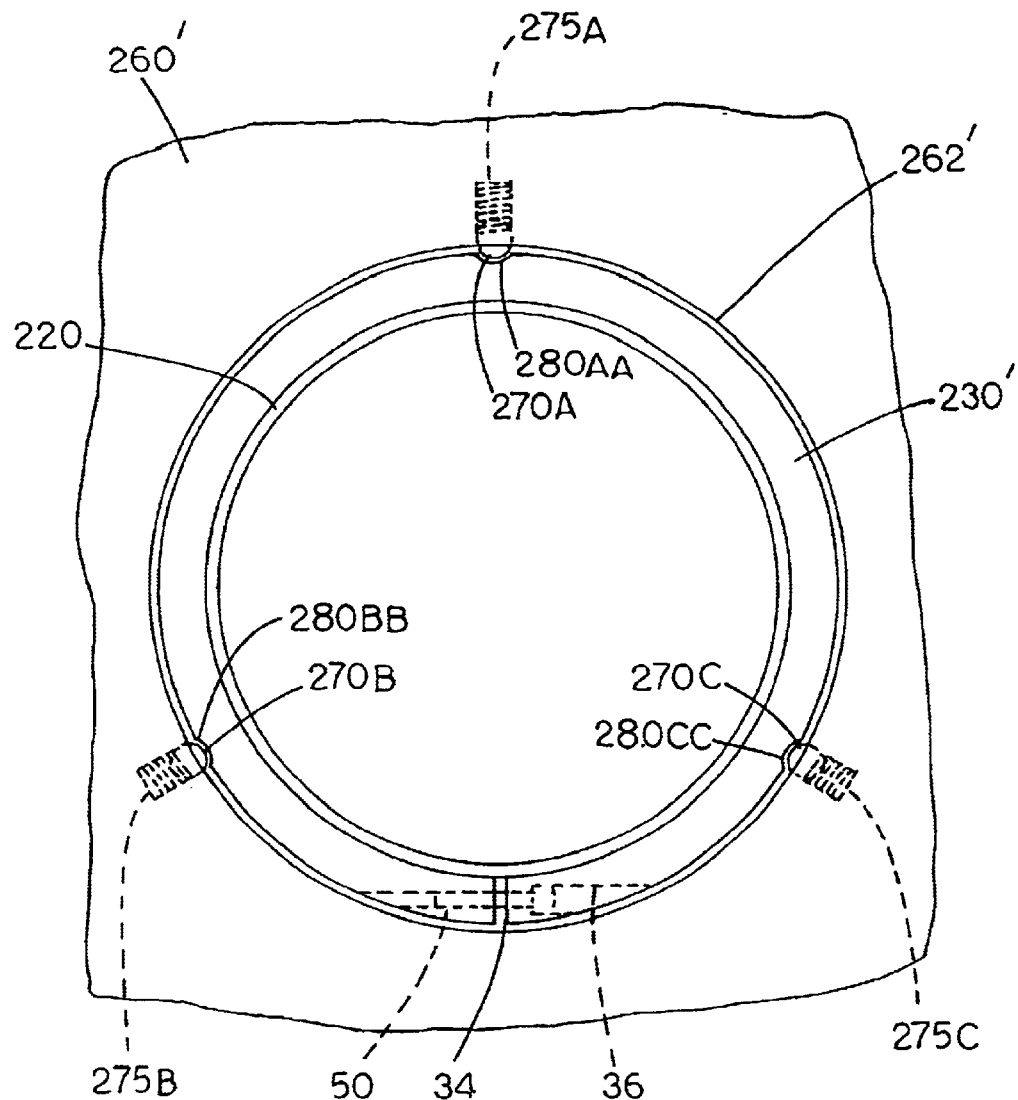
FIG. 7B is a top plan view of the vessel centering system according to another embodiment of the present invention wherein biased radial members are oriented differently from those radial members illustrated in FIG. 7A.

Referring to FIG. 7B, the respective orientations of bearings 270A, 270B and 270C and their associated biasing mechanisms 275A, 275B and 275C have been inverted such that they are radially inwardly biased toward a flanged section 230' (which can be integrally manufactured with vessel 220 or provided as a separate, removable component as in other embodiments discussed above). Each bearing 270A, 270B and 270C and its associated biasing mechanism 275A, 275B and 275C are supported in or by a vessel plate 260'. Hence, bearings 270A, 270B and 270C extend inwardly from an aperture 262' of vessel plate 260' and are biased to make contact with flanged section 230' to establish the concentricity of vessel 220. As in the embodiment illustrated in FIG. 7A, neither flanged section 230' nor aperture 262' require an annular gap 45 (or 145). However, conformingly-shaped depressions or recesses 280AA, 280BB and 280CC may be provided along the outer diameter of flanged section 230' at the respective locations of bearings 270A, 270B and 270C to at least partially receive the outer profile of bearings 270A, 270B and 270C.

Referring to FIG. 8, a further alternative embodiment of the present invention is illustrated in which a vessel centering or alignment system, generally designated 300, takes advantage of magnetic attractive forces for the purpose of properly centering or aligning vessel 20. As in previously described embodiments, a multi-part system is provided in which an annular or ring member, generally designated 310, is fitted in a circumferential groove 24 formed around a peripheral section of vessel wall 22. As before, one or more tangential screws 50 and corresponding structural features (or other fastener elements such as clamps) can be employed to secure ring member 310 to groove 24. In this particular embodiment, one or more magnetic elements 312 are provided with system 300 to interact with complementary magnetic elements supported in the vicinity of the apertures in which each such system 300 is to be mounted or installed. In the preferred embodiment illustrated in FIG. 8, ring member 310 includes mounting bores 314 in which magnetic elements 312 are disposed. In the specific embodiment illustrated in FIG. 8, ring member 310 comprises two parts: an upper part or ring member generally designated 310A, and a lower part or ring member generally designated 310B. Magnetic element or elements 312 could be mounted to or supported by either upper ring member 310A or lower ring member 310B. In the illustrated embodiment, magnetic elements 312 are disposed in mounting bores 314 of lower ring member 310B, and upper ring member 310A is placed in removable contact with lower ring member 310B to cover the exposed top surfaces of magnetic elements 312 and thereby effect a complete enclosure of magnetic elements 312.

Figure 9:
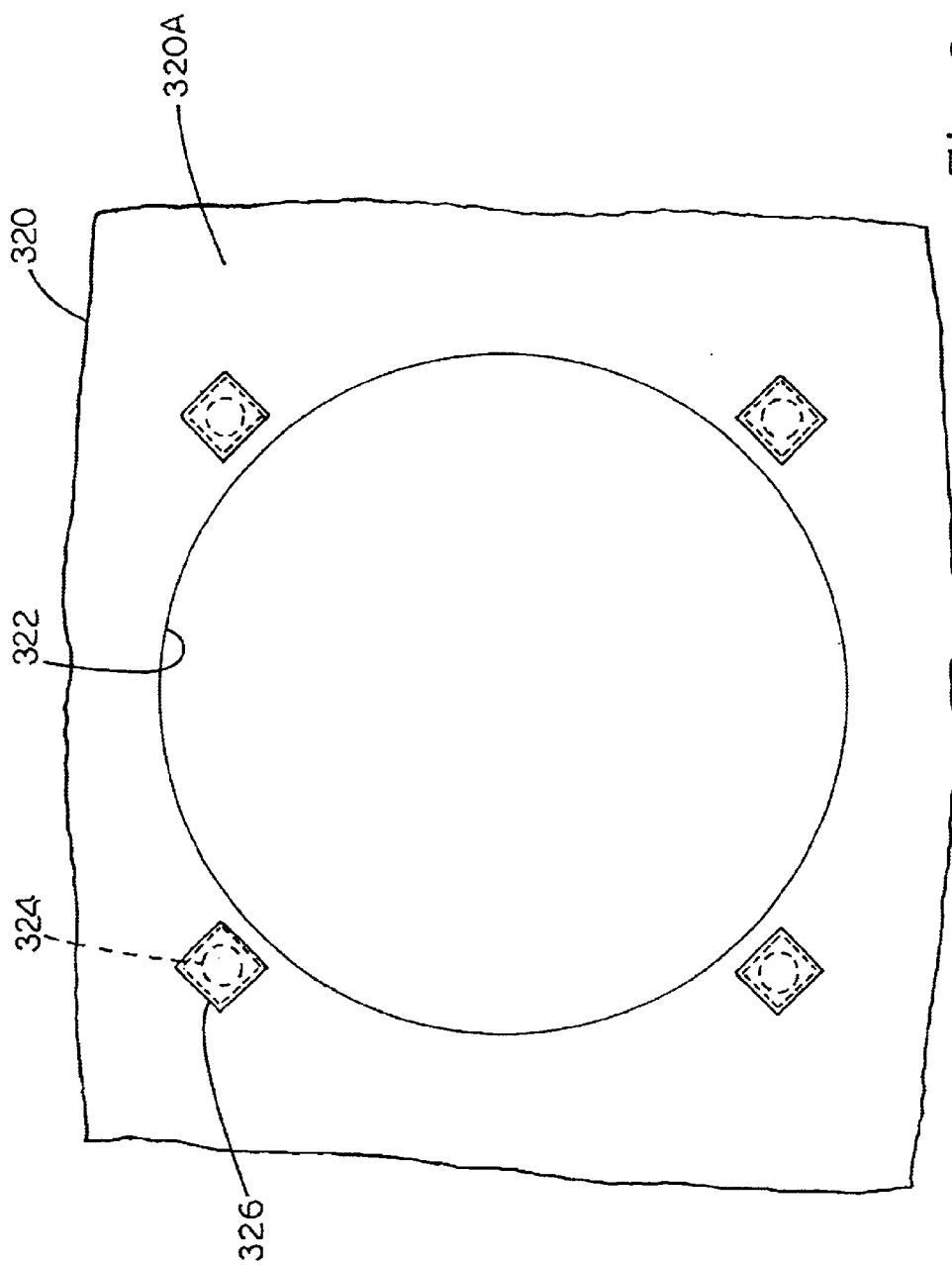
FIG. 9 is a bottom plan view of a region of a vessel plate containing magnets to accommodate the mounting of the vessel centering system illustrated in FIG. 8.

Proper alignment or centering can be achieved by causing magnetic elements 312 supported by ring member 310 to interact with complementary magnetic elements supported in the vicinity of the apertures or mounting holes of a vessel plate. Referring to FIG. 9, the underside of one section of a vessel plate 320 surrounding an aperture 322 of vessel plate 320 is illustrated. One or more magnetic elements 324 (illustrated in phantom) are supported by vessel plate 320 and situated around the periphery of each aperture 322 of vessel plate 320. In the specific embodiment shown in FIG. 9, magnetic elements 324 are housed in mounting blocks 326 that depend from a bottom surface 320A of vessel plate 320. Mounting blocks 326 could be formed with vessel plate 320, or alternatively be provided as separate components that are attached to bottom surface 320A. Magnetic elements 324 supported by vessel plate 320 are precisely positioned such that, upon insertion or installation of each vessel 20 into each aperture 322, each magnetic element 324 is attracted by magnetic force to a corresponding one of magnetic elements 312 supported by ring member 310 (see FIG. 8). As a result, the magnetic attraction causes vessel 20 with ring member 310 to rotate and/or translate until each magnetic element 312 of ring member 310 becomes coaxially aligned with each corresponding magnetic element 324 of vessel plate 320, with the axis of alignment being each central longitudinal axis of each pair of magnetic elements 312 and magnetic elements 324. After this self-centering or self-alignment occurs, vessel 20 is held in a properly centered position under the influence of the magnetic forces localized with respect to each pair of magnetic elements 312 and 324.

Figure 10:
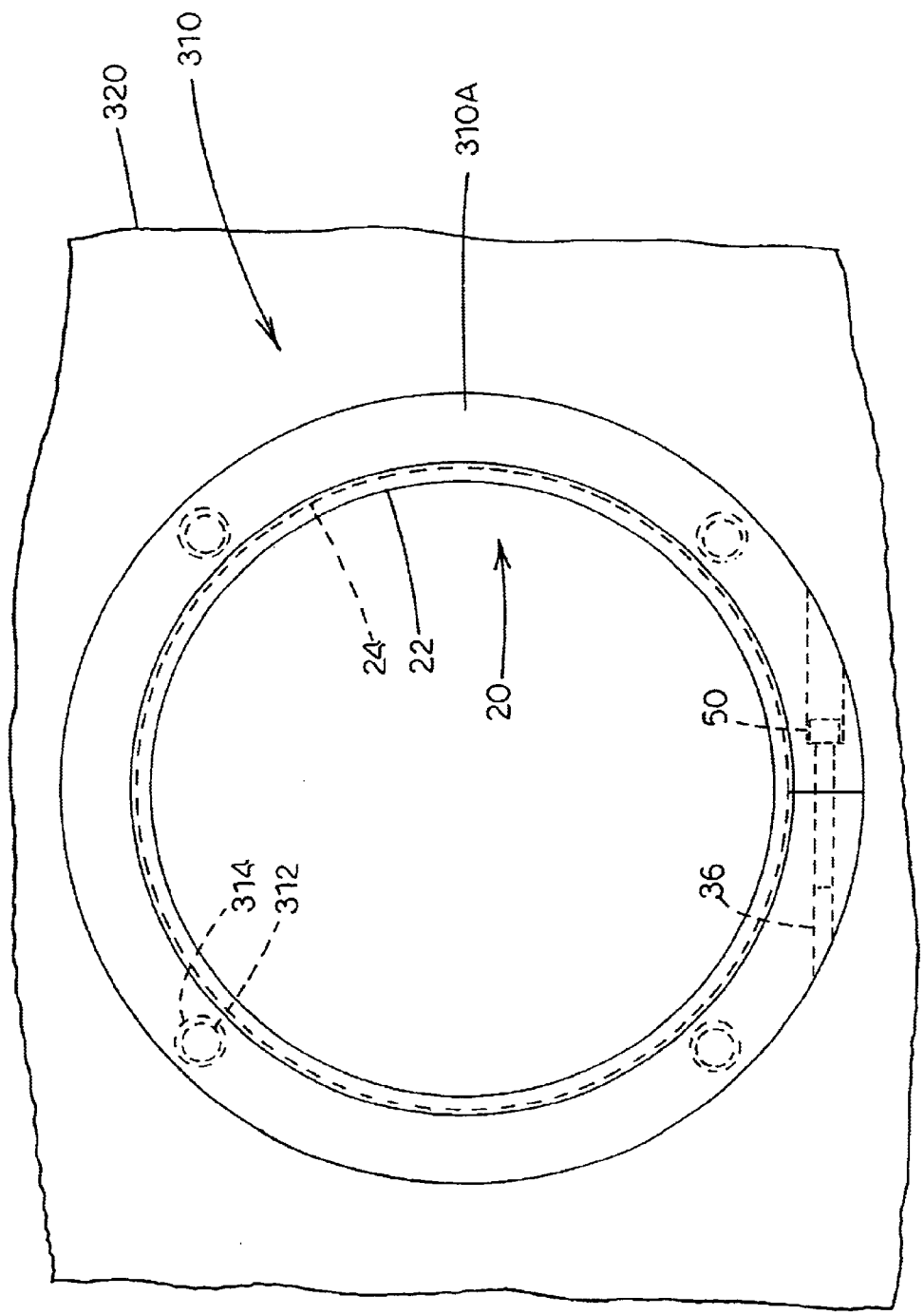
FIG. 10 is a top plan view of the vessel centering system illustrated in FIG. 8 mounted in the vessel plate illustrated in FIG. 9.
Figure 11:
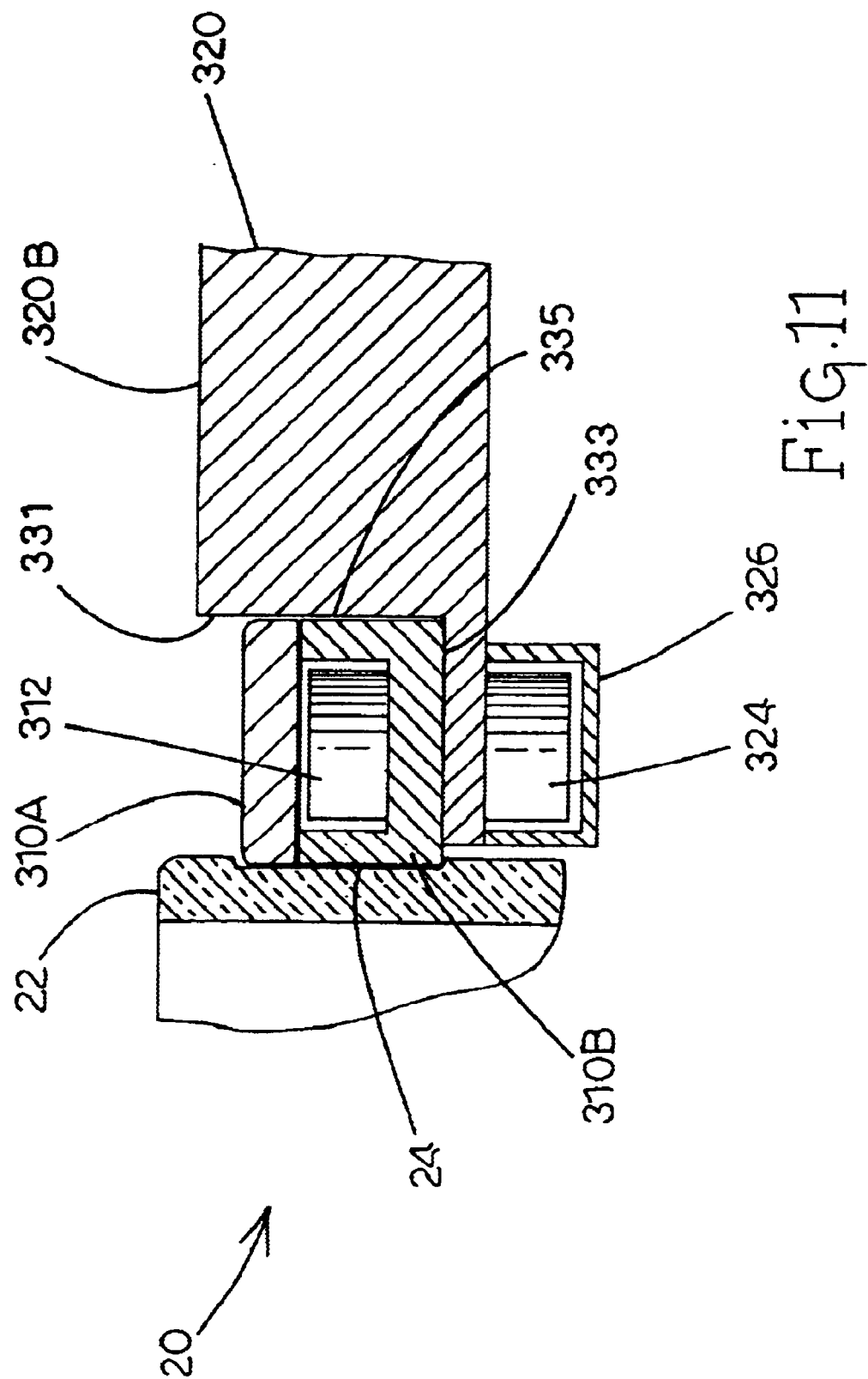
FIG. 11 is a detailed vertical cross-sectional and partial cut-away view of the embodiment of the vessel centering system illustrated in FIGS. 8–10, and showing the interaction of a pair of magnets in accordance with the present invention.

FIG. 10 is a top view of a section of vessel plate 320, in which vessel 20 has been installed in one aperture 322 of vessel plate 320 and self-alignment has occurred. The partially cutaway cross-sectional view in FIG. 11 also shows this alignment resulting from magnetic attraction, as well as the proximity of one pair of magnetic elements 312 and 324 to each other and their co-alignment with each other. FIG. 11 further shows that, instead of disposing ring member 310 on a topmost surface 320B of vessel plate 320, ring member 310 can be disposed in a shoulder 331 of vessel plate 320 defined by a horizontal surface 333 and a vertical or lateral surface 335 of vessel plate 320.

Figure 12:
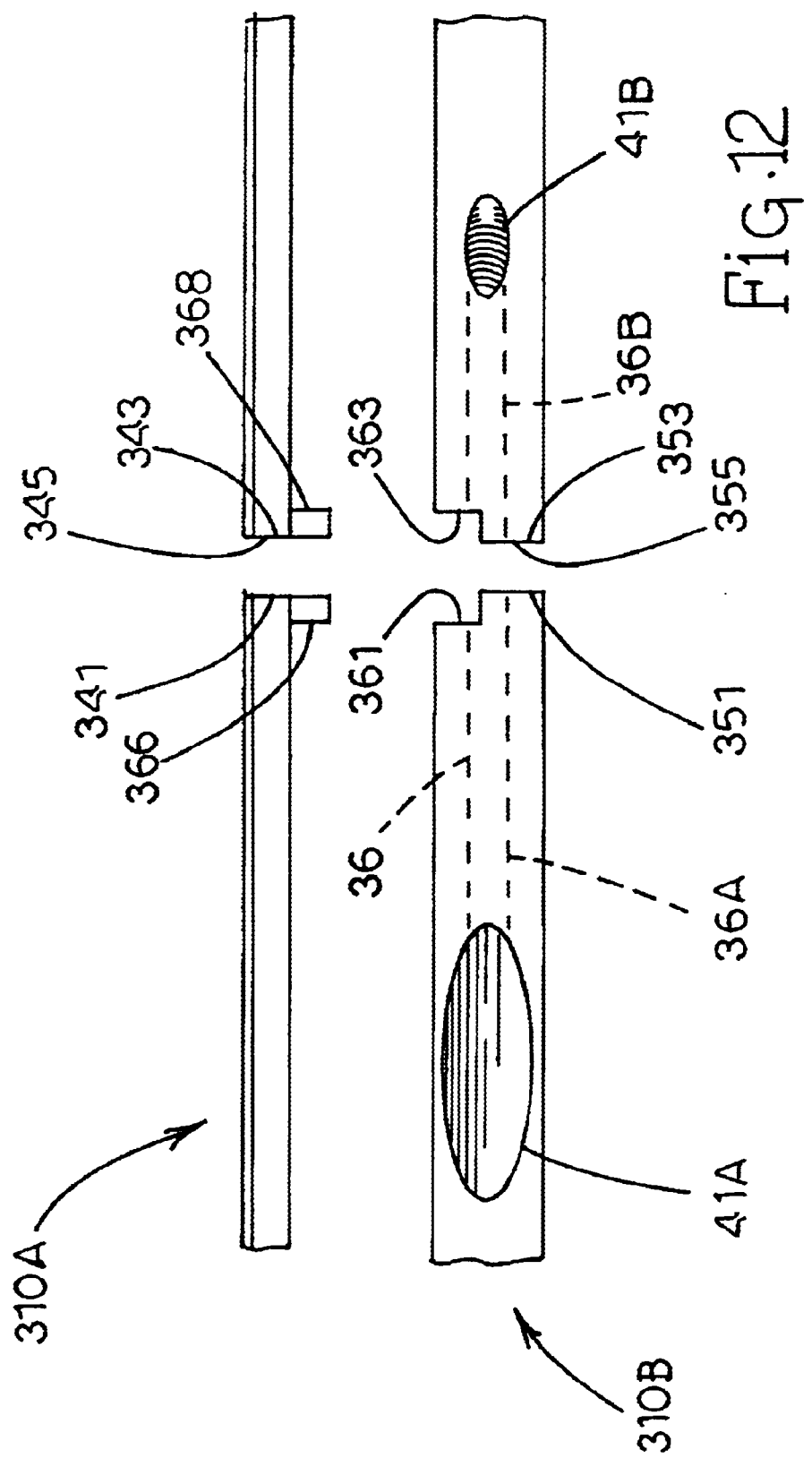
FIG. 12 is a front elevation view of a section of a two-part vessel alignment ring provided in accordance with the present invention.

Referring to FIG. 12, some details are illustrated of ring member 310 when provided in two-part form. Upper ring member 310A terminates at two lateral end surfaces 341 and 343, respectively, which are separated by an upper gap 345. Similarly, lower ring member 310B terminates at two lateral end surfaces 351 and 353, respectively, which are separated by a lower gap 355. When upper ring member 310A is brought into contact with lower ring member 310B, upper gap 345 is generally aligned with lower gap 355 to form a single gap, the width of which can be varied by adjusting tangential screw 50 within tangential bore 36 having first and second bore sections 36A and 36B and outer apertures 41A and 41B, respectively. In the specific embodiment shown in FIG. 12, each lateral end surface 351 and 353 of lower ring member 310B is profiled to define a respective shoulder 361 and 363, such that lower gap 355 has a stepped profile. This configuration is useful for receiving protrusions 366 and 368 that depend from upper ring member 310A at or near its lateral end surfaces 341 and 343. When upper ring member 310A is mounted onto lower ring member 310B, protrusions 366 and 368 respectively engage shoulders 361 and 363. Accordingly, the effect of tangential screw 50 in urging lateral end surfaces 351 and 353 of lower ring member 310B towards each other is to likewise urge lateral end surfaces 341 and 343 of upper ring member 310A towards each other. Protrusions 366 and 368 are dimensioned so as not to interfere with first and second sections 36A and 36B of tangential bore 36.

It will be understood that the interfacial features of upper ring member 310A and lower ring member 310B could alternatively be inverted. That is, tangential bore 36 and its related structural features could be formed on upper ring member 310A instead of lower ring member 310B, lower ring member 310B could define the stepped gap, and protrusions 366 and 368 could extend from lower ring member 310B to engage the surfaces defining the stepped gap of upper ring member 310A. Moreover, magnetic elements 312 could be supported by upper ring member 310A rather than by lower ring member 310B.

Figure 13:
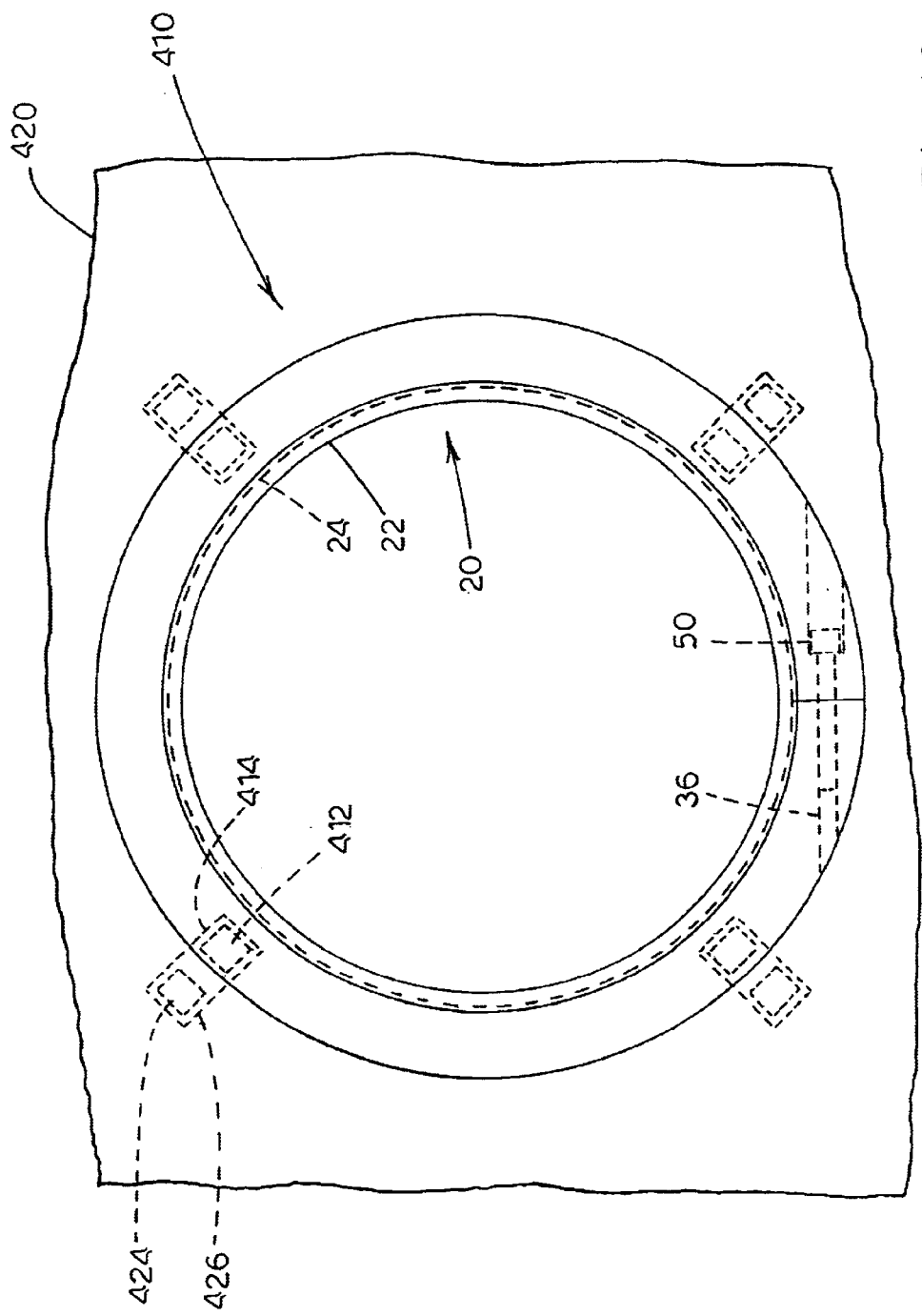
FIG. 13 is a top plan view of a vessel centering system mounted in a vessel plate in accordance with a further embodiment of the present invention.

Referring now to FIG. 13, a further alternative embodiment of the present invention is illustrated in which a ring member, generally designated 410, has been fitted to vessel 20 and the system installed in a vessel plate 420. In this particular embodiment, ring member 410 supports one or more radially-oriented magnetic elements 412, such as in mounting bores 414, and vessel plate 410 supports radially-oriented magnetic elements 424 such as in mounting bores 426. Due to the magnetic attraction between corresponding pairs of magnetic elements 412 and 424, self-centering or self-alignment of vessel 20 occurs and magnetic elements 412 and 424 radially oppose each other. It should be noted that in this embodiment, magnetic elements 412 and 424 are disposed along axes generally perpendicular or transverse to longitudinal axis L (see FIG. 8) of vessel 20. By contrast, in the embodiment shown in FIGS. 8–11, magnetic elements 312 and 324 are disposed along axes generally parallel with longitudinal axis L of vessel 20.

It can therefore be seen from the foregoing description that the present invention provides a useful system for centering and aligning a vessel with respect to a stirring element or other elongate instrument intended to operate within such vessel.

It will be understood that various details of the invention may be changed without departing from the scope of the invention. Furthermore, the foregoing description is for the purpose of illustration only, and not for the purpose of limitation-the invention being defined by the claims.

What is claimed is:

1. A vessel adapted for improved centering with respect to a spindle or other instrument when installed in a vessel plate, the vessel comprising:

(a) a vessel wall including an outer surface and a vessel groove formed on a circumference of the vessel outer surface;

(b) a ring member fitted in the vessel groove and extending outwardly with respect to the vessel wall; and (c) a magnetic element supported by the ring member.

2. The vessel according to claim 1 wherein the ring member terminates at a first lateral end surface and at a second lateral end surface, and a gap is defined between the first and second lateral end surfaces.

3. The vessel according to claim 2 comprising a fastening element engaging the ring member at the first and the second lateral end surfaces.

4. The vessel according to claim 1 wherein the ring member includes a plurality of segments, each segment having a lateral end surface spaced at a distance from an adjacent lateral end surface of at least one other segment, and wherein a plurality of gaps are defined between respective spaced lateral end surfaces of adjacent segments, and a plurality of fastening elements respectively engage the spaced lateral end surfaces of the adjacent segments.

5. The vessel according to claim 1 wherein the ring member includes upper and lower portions, the lower portion includes a recess, the magnetic element is disposed in the recess, and the upper portion contacts the lower portion to enclose the magnetic element.

6. The vessel according to claim 5 wherein the upper portion of the ring member terminates at first and second upper portion end surfaces, an upper portion gap is defined between the first and second upper portion end surfaces, the lower portion of the ring member terminates at first and second lower portion end surfaces, a lower portion gap is defined between the first lower portion and the second lower portion end surfaces, and the upper portion gap is generally aligned with the lower portion gap.

7. The vessel according to claim 6 wherein the upper portion of the ring member includes a first protrusion extending into the lower portion gap in contact with the first lower portion end surface, and a second protrusion extending into the lower portion gap in contact with the second lower portion end surface.

8. The vessel according to claim 6 comprising a fastening element engaging the lower portion of the ring member at the first and second lower portion end surfaces.

9. The vessel according to claim 6 wherein the lower portion of the ring member includes a first protrusion extending into the upper portion gap in contact with the first upper portion end surface, and a second protrusion extending into the upper portion gap in contact with the second upper portion end surface.

10. The vessel according to claim 6 comprising a fastening element engaging the upper portion of the ring member at the first and second upper portion end surfaces.

11. A vessel adapted for improved centering with respect to a spindle or other instrument when installed in a vessel plate, the vessel comprising:
   (a) a vessel wall including an outer surface and a vessel groove formed on a circumference of the vessel outer surface;
   (b) a ring member fitted in the vessel groove and extending outwardly with respect to the vessel wall, the ring member terminating at a gap defined by a first lateral end surface of the ring member and a second lateral end surface of the ring member;
   (c) a magnetic element supported by the ring member; and
   (d) a fastening element engaging the ring member at the first and second lateral end surfaces.

12. A vessel adapted for improved centering with respect to a spindle or other instrument when installed in a vessel plate, the vessel comprising:
   (a) a vessel wall including an outer surface and a vessel groove formed on a circumference of the vessel outer surface;
   (b) an upper ring member fitted in the vessel groove and extending outwardly with respect to the vessel wall, the upper ring member terminating at a first upper ring member end surface and a second upper ring member end surface, wherein an upper gap is defined between the first and second upper ring member end surfaces;
   (c) a lower ring member fitted in the vessel groove in adjacent contact with the upper ring member and extending outwardly with respect to the vessel wall, the lower ring member terminating at a first lower ring member end surface and a second lower ring member end surface, wherein a lower gap is defined between the first and second lower ring member end surfaces and is substantially aligned with the upper gap;
   (d) a magnetic element mounted to the lower ring member and covered by the upper ring member; and
   (e) a fastening element extending between the first and second end surfaces of the upper and lower ring members.

13. The vessel according to claim 12 wherein the upper ring member includes a first protrusion extending into the lower gap in contact with the first lower ring member end surface, and a second protrusion extending into the lower portion gap in contact with the second lower ring member end surface.

14. A vessel adapted to be centered with respect to a spindle or other instrument when installed in a vessel plate, the vessel comprising:
   (a) a vessel wall including an outer surface and a vessel groove formed on a circumference of the vessel outer surface;
   (b) a ring member fitted in the vessel groove and extending outwardly with respect to the vessel, the ring member including an outer surface, a first lateral end surface, a second lateral end surface, a first tangential bore extending from a first outer aperture of the ring member outer surface to a first inner aperture of the first lateral end surface, and a second tangential bore extending from a second outer aperture of the ring member outer surface to a second inner aperture of the second lateral end surface, wherein the first and second lateral end surfaces define a gap therebetween, and wherein the first and second tangential bores extend along a line generally tangential to a curvature of the ring member;
   (c) a magnetic element supported by the ring member; and
   (d) a fastening element disposed in the first and second tangential bores, the fastening element extending through the first inner aperture, across the gap, and through the second inner aperture, wherein the fastening element is movable along the generally tangential line of the first and second tangential bores in engagement with the ring member.

15. The vessel according to claim 14 wherein at least one of the tangential bores includes a threaded section, and the fastening element is threaded for mating engagement with the threaded section.

16. A vessel centering system comprising:
   (a) a vessel including an outer surface and a vessel groove formed on a circumference of the vessel outer surface;
   (b) an annular spacer member fitted in the vessel groove and extending outwardly with respect to the vessel
   (c) a magnetic element supported by the spacer member; and
   (d) means for tightening the spacer member against the vessel groove.

17. The vessel centering system according to claim 16, wherein the tightening means includes a tangential bore formed in the spacer member and a fastening means disposed in adjustable engagement with the spacer member at the tangential bore, and wherein the tangential bore extends along a line generally tangential to a curvature of the spacer member.

18. The vessel centering system according to claim 17, wherein the spacer member includes an outer surface, a first lateral end surface and a second lateral end surface, the first and second lateral end surfaces defining a spacer gap therebetween.

19. The vessel centering system according to claim 18 wherein:
   (a) the tangential bore of the spacer member includes a first tangential bore section extending from a first outer aperture of the spacer member outer surface to a first inner aperture of the first lateral end surface, and a second tangential bore section extending from a second outer aperture of the spacer member outer surface to a second inner aperture of the second lateral end surface; and
   (b) the fastening means includes a fastening element disposed in the first and second tangential bore sections, the fastening element extending through the first inner aperture, across the spacer gap, and through the second inner aperture, wherein the fastening element is adjustable along the generally tangential line of the first and second tangential bore sections to adjust a tightness of the fit of the spacer member in the vessel groove.

20. The vessel centering system according to claim 16 wherein the spacer member includes an upper portion and a lower portion disposed in engagement with the upper portion.

21. A vessel centering system comprising:
(a) a vessel plate including a first magnetic element and a vessel plate aperture;
(b) a vessel extending through the vessel plate aperture, the vessel including an outer surface and a vessel groove formed on a circumference of the vessel outer surface;
(c) an annular spacer member fitted in the vessel groove and disposed on the vessel plate; and
(d) a second magnetic element supported by the spacer member and aligned with the first magnetic element by magnetic attraction.

22. The vessel centering system according to claim 21 wherein the vessel plate aperture includes a first edge and a second edge, the first and second edges cooperatively defining an annular shoulder, and the spacer member is disposed on the first edge.

23. The vessel centering system according to claim 22 wherein the first magnetic element is supported by the vessel plate at a location below the first edge of the vessel plate aperture.

24. The vessel centering system according to claim 23 comprising a mounting block extending from the vessel plate at a location proximate to the first edge of the vessel plate aperture, wherein the first magnet is supported by the mounting block.

25. The vessel centering system according to claim 22 wherein the second edge of the vessel plate aperture is generally parallel with a longitudinal axis of the vessel, and the first magnetic element is disposed in the vessel plate at a radially outward distance from the longitudinal axis.

26. The vessel centering system according to claim 21 wherein the vessel plate includes an upper side, a bottom side opposing the upper side, and a mounting block extending from the bottom side, and wherein the first magnetic element is supported by the mounting block and the spacer member is disposed on the upper side.

27. The vessel centering system according to claim 21 comprising a fastening element, wherein the spacer member terminates at a first lateral end surface and a second lateral end surface and the fastening element engages the spacer member at the first and second lateral end surfaces.

28. The vessel centering system according to claim 27 wherein the spacer member includes an outer surface, a first tangential bore extending from a first outer aperture of the spacer member outer surface to a first inner aperture of the first lateral end surface, and a second tangential bore extending from a second outer aperture of the spacer member outer surface to a second inner aperture of the second lateral end surface, the first and second lateral end surfaces defining a gap therebetween, and the first and second tangential bores extending along a line generally tangential to a curvature of the spacer member.

29. The vessel centering system according to claim 28 wherein the fastening element is disposed in the first and second tangential bores and extends through the first inner aperture, across the gap and through the second inner aperture, and wherein the fastening element is adjustable along the generally tangential line of the first and second tangential bores to adjust a tightness of the fit of the spacer member in the vessel groove.

30. The vessel centering system according to claim 21 wherein the vessel outer surface is coaxially disposed about a longitudinal axis of the vessel, and the first and second magnetic elements are co-aligned with each other along a direction generally parallel with the longitudinal axis.

31. The vessel centering system according to claim 21 wherein the vessel outer surface is coaxially disposed about a longitudinal axis of the vessel, and the first and second magnetic elements are co-aligned with each other along a direction generally perpendicular to the longitudinal axis.

32. A method for aligning a vessel concentrically with respect to a shaft extending into the vessel, comprising the steps of:
(a) providing a flangeless vessel body having a groove formed circumferentially around an outer surface of the vessel;
(b) fitting an annular spacer member in the vessel groove, the spacer member including a first magnetic element, wherein the vessel body and the spacer member cooperatively form a multi-piece flanged vessel; and
(c) securing the spacer member in the vessel groove by utilizing a fastening element engaging the spacer member.

33. The method according to claim 32 comprising the step of installing the vessel in an aperture of a vessel plate, the vessel plate including a second magnetic element, wherein magnetic attraction between the first and second magnetic elements causes the vessel to become aligned in the aperture.

34. The method according to claim 32 comprising the step of providing the spacer member in two-part form, wherein a first part of the spacer member contacts a second part of the spacer member, and the first magnetic element is enclosed by the first and second parts.

35. The method according to claim 32 wherein the step of fitting the spacer member in the vessel groove includes using a fastener element to engage the spacer member.

* * * * *